US012408836B2

United States Patent
Li et al.

(10) Patent No.: US 12,408,836 B2
(45) Date of Patent: Sep. 9, 2025

(54) METHOD AND SYSTEM FOR EXTRACTING MULTI-DIMENSIONAL DISCONNECTION NETWORK REGION OF SYMPTOM MAPPING

(71) Applicants: Beijing Tiantan Hospital, Capital Medical University, Beijing (CN); Beihang University, Beijing (CN)

(72) Inventors: Zixiao Li, Beijing (CN); Tao Liu, Beijing (CN); Hao Liu, Beijing (CN); Lingling Ding, Beijing (CN); Yongjun Wang, Beijing (CN)

(73) Assignees: Beijing Tiantan Hospital, Capital Medical University (CN); Beihang University (CN)

( * ) Notice: Subject to any disclaimer, the term of this patent is extended or adjusted under 35 U.S.C. 154(b) by 300 days.

(21) Appl. No.: 18/163,425

(22) Filed: Feb. 2, 2023

(65) Prior Publication Data

US 2024/0046454 A1 Feb. 8, 2024

(30) Foreign Application Priority Data

Aug. 2, 2022 (CN) .......................... 202210918696.0

(51) Int. Cl.
*A61B 5/00* (2006.01)
*G06T 7/00* (2017.01)
*G06T 7/73* (2017.01)

(52) U.S. Cl.
CPC .......... *A61B 5/0042* (2013.01); *A61B 5/4064* (2013.01); *A61B 5/7425* (2013.01);
(Continued)

(58) Field of Classification Search
CPC ..... A61B 5/055; A61B 5/0033; A61B 5/0042; G06T 7/0012; G06T 7/73; G06T 7/246;
(Continued)

(56) References Cited

PUBLICATIONS

Salvalaggio, Alessandro, et al. "Post-stroke deficit prediction from lesion and indirect structural and functional disconnection." Brain 143.7 (2020): 2173-2188.*

(Continued)

*Primary Examiner* — Carolyn A Pehlke
(74) *Attorney, Agent, or Firm* — Weisberg I.P. Law, P.A.

(57) ABSTRACT

A method and system for extracting a multi-dimensional disconnection network region of symptom mapping: registering a lesion image to a brain standard space; obtaining diffusion magnetic resonance images and resting-state functional magnetic resonance images of healthy control groups; constructing a structural disconnection weighting network corresponding to lesions using a fiber tracking method according to the lesion image in the brain standard space and the diffusion magnetic resonance images; constructing a functional significant disconnection network corresponding to the lesions using a cross-correlation verification method according to the lesion image in the brain standard space and the resting-state functional magnetic resonance images; and determining the multi-dimensional disconnection network region of the lesions of symptom mapping according to the structural disconnection weighting network and the functional significant disconnection network, where the multi-dimensional disconnection network region of the lesions is configured to locate network mapping of a brain lesion in the brain.

8 Claims, 7 Drawing Sheets

(52) U.S. Cl.
CPC .............. *G06T 7/0012* (2013.01); *G06T 7/73* (2017.01); *G06T 2207/10088* (2013.01); *G06T 2207/30016* (2013.01)

(58) Field of Classification Search
CPC .............. G06T 7/33; G06T 2207/10088; G06T 2207/30016
See application file for complete search history.

(56) References Cited

PUBLICATIONS

Boes, Aaron D., et al. "Network localization of neurological symptoms from focal brain lesions." Brain 138.10 (2015): 3061-3075.*

* cited by examiner

METHOD AND SYSTEM FOR EXTRACTING MULTI-DIMENSIONAL DISCONNECTION NETWORK REGION OF SYMPTOM MAPPING

CROSS-REFERENCE TO RELATED APPLICATION

This application claims priority to Chinese Patent Application No. 202210918696.0, filed on Aug. 2, 2022, entitled "METHOD AND SYSTEM FOR EXTRACTING MULTI-DIMENSIONAL DISCONNECTION NETWORK REGION OF SYMPTOM MAPPING", the entirety of which is incorporated herein.

FIELD

The present disclosure relates to the field of medical images, and in particular, to a method and system for extracting a multi-dimensional disconnection network region of symptom mapping.

BACKGROUND

Brain lesions, including stroke lesions, can cause multi-dimensional cognitive and behavioral impairment of human body. However, the specific mechanism of how brain lesions affect cognitive and behavioral functions remains unclear. Studying the mapping relationship between brain lesions and symptoms is expected to improve the understanding of the pathological mechanism of clinical neurological diseases and provide a new and effective intervention plan for the treatment and rehabilitation of neurological diseases.

The existing lesion-symptom mapping analysis technology is usually single lesion analysis, which is also the traditional analysis technology in this field. This technology studies the mapping relationship between lesions and symptoms by locating the corresponding lesions of a symptom. Early lesion studies were based on autopsy and pre-life disease records to analyze the mapping relationship between symptoms. With the maturity of non-invasive imaging technology, recent technologies have begun to use neuroimaging tools for correlation analysis of lesions and symptoms. Several classic technical achievements have found that the left frontal lobe injury has a significant impact on language production. The injury of medial temporal lobe is related to memory function. This analysis technique can also make some possible causal hypothesis inferences, providing indirect experimental support for locating clinical therapeutic targets. These results show that the mapping relationship between lesions and symptoms is indeed true, and imaging technology also provides a powerful tool for this analysis.

Although the existing single-lesion symptom mapping analysis technology has found many classic mapping relationships, there is a lot of evidence that this analysis technology based on lesion location will be flawed. This is because sometimes similar lesions may be related to injuries at multiple different brain locations. Even if the lesions overlap among patients with the same symptoms, the overlapping location may not conform to the traditional concept of the function of this part of the brain. For example, the brain stem injury that leads to hallucination is generally located in the midbrain and medial thalamus, but there is no obvious evidence related to vision or visual imagery in these areas. The result of this defect means that the relationship between the symptoms and the location of the lesion may also be indirect. Therefore, the simple use of a single lesion analysis method may lead to the misjudgment of the "lesion-symptom" relationship.

SUMMARY

An objective of the present disclosure is to provide a method and system for extracting a multi-dimensional disconnection network region of symptom mapping, so as to solve the problem of low accuracy of "lesion-symptom" relationship.

To achieve the above objective, the present disclosure provides the following technical solutions:

A method for extracting a multi-dimensional disconnection network region of symptom mapping includes:
  obtaining a lesion image, and registering the lesion image to a brain standard space;
  using brain images of healthy people with multiple ages and a balanced sex ratio as healthy control groups, and obtaining diffusion magnetic resonance images and resting-state functional magnetic resonance images of the healthy control groups;
  constructing a structural disconnection weighting network corresponding to lesions using a fiber tracking method according to the lesion image in the brain standard space and the diffusion magnetic resonance images, where the fiber tracking method includes deterministic fiber tracking and probabilistic fiber tracking;
  constructing a functional significant disconnection network corresponding to the lesions using a cross-correlation verification method according to the lesion image in the brain standard space and the resting-state functional magnetic resonance images; and
  determining the multi-dimensional disconnection network region of the lesions of symptom mapping according to the structural disconnection weighting network and the functional significant disconnection network, where the multi-dimensional disconnection network region of the lesions is configured to locate network mapping of a brain lesion in the brain.

Optionally, a process of registering the lesion image to a brain standard space specifically includes:
  registering the lesion image to the brain standard space through linear transformation.

Optionally, a process of constructing a structural disconnection weighting network corresponding to lesions using a fiber tracking method according to the lesion image in the brain standard space and the diffusion magnetic resonance images specifically includes:
  performing pre-processing and diffusion weighted imaging modeling on the diffusion magnetic resonance images, and performing fiber tracking using the fiber tracking method to construct deterministic and probabilistic fiber tracking structural connection images in individual spaces of the healthy control groups;
  registering the lesion image in the brain standard space to an individual space of the healthy control group through linear transformation for any of the healthy control groups, and extracting a structural connection image of the lesions according to the deterministic and probabilistic fiber tracking structural connection images;
  calculating a weighted average of the structural connection image of the lesions to determine a structural disconnection weighting network in the individual spaces;

registering the structural disconnection weighting network in the individual spaces to the brain standard space through linear transformation to determine a structural disconnection weighting network of the lesions corresponding to the healthy control groups; and constructing the structural disconnection weighting network corresponding to the lesions according to the structural disconnection weighting network of the lesions corresponding to all of the healthy control groups.

Optionally, a process of constructing a functional significant disconnection network corresponding to the lesions using a cross-correlation verification method according to the lesion image in the brain standard space and the resting-state functional magnetic resonance images specifically includes:

pre-processing the resting-state functional magnetic resonance images to determine a brain functional signal image in the brain standard space;

extracting an average signal of a range of the lesions by taking the lesion image as a region of interest (ROI) in the brain standard space;

performing Pearson correlation between the average signal and signals of the rest of the whole brain based on the brain functional image to determine a functional connection value between the whole brain and a lesion region;

calculating cross-correlation and out-of-order correlation values between the average signal and the signals of the rest of the whole brain using the cross-correlation verification method;

retaining a cross-correlation value more than 100 times the out-of-order correlation value as a first cross-correlation value, and taking a functional connection value of a position corresponding to the first cross-correlation value as a functional significant disconnection network of the lesions corresponding to the healthy control groups; and constructing the functional significant disconnection network corresponding to the lesions according to the functional significant disconnection network of the lesions corresponding to all of the healthy control groups.

A system for extracting a multi-dimensional disconnection network region of symptom mapping includes:

a registration module configured to obtain a lesion image, and register the lesion image to a brain standard space;

an image obtaining module configured to use brain images of healthy people with multiple ages and a balanced sex ratio as healthy control groups, and obtain diffusion magnetic resonance images and resting-state functional magnetic resonance images of the healthy control groups;

a structural disconnection weighting network construction module corresponding to lesions configured to construct a structural disconnection weighting network corresponding to lesions using a fiber tracking method according to the lesion image in the brain standard space and the diffusion magnetic resonance images, where the fiber tracking method includes deterministic fiber tracking and probabilistic fiber tracking;

a functional significant disconnection network construction module corresponding to lesions configured to construct a functional significant disconnection network corresponding to the lesions using a cross-correlation verification method according to the lesion image in the brain standard space and the resting-state functional magnetic resonance images; and a multi-dimensional disconnection network region determination module of lesions configured to determine the multi-dimensional disconnection network region of the lesions of symptom mapping according to the structural disconnection weighting network and the functional significant disconnection network, where the multi-dimensional disconnection network region of the lesions is configured to locate network mapping of a brain lesion in the brain.

Optionally, the registration module specifically includes:

a registration unit configured to register the lesion image to the brain standard space through linear transformation.

Optionally, the structural disconnection weighting network construction module corresponding to lesions specifically includes:

a deterministic and probabilistic fiber tracking structural connection image construction unit configured to perform pre-processing and diffusion weighted imaging modeling on the diffusion magnetic resonance images, and perform fiber tracking using the fiber tracking method to construct deterministic and probabilistic fiber tracking structural connection images in individual spaces of the healthy control groups;

a structural connection image extraction unit of lesions configured to register the lesion image in the brain standard space to an individual space of the healthy control group through linear transformation for any of the healthy control groups, and extract a structural connection image of the lesions according to the deterministic and probabilistic fiber tracking structural connection images;

a structural disconnection weighting network determination unit in individual spaces configured to calculate a weighted average of the structural connection image of the lesions to determine a structural disconnection weighting network in the individual spaces;

a structural disconnection weighting network determination unit of lesions corresponding to healthy control groups configured to register the structural disconnection weighting network in the individual spaces to the brain standard space through linear transformation to determine a structural disconnection weighting network of the lesions corresponding to the healthy control groups; and a structural disconnection weighting network construction unit corresponding to lesions configured to construct the structural disconnection weighting network corresponding to the lesions according to the structural disconnection weighting network of the lesions corresponding to all of the healthy control groups.

Optionally, the functional significant disconnection network construction module corresponding to lesions specifically includes:

a brain functional signal image determination unit configured to pre-process the resting-state functional magnetic resonance images to determine a brain functional signal image in the brain standard space;

an average signal extraction unit configured to extract an average signal of a range of the lesions by taking the lesion image as a ROI in the brain standard space;

a functional connection value determination unit configured to perform Pearson correlation between the average signal and signals of the rest of the whole brain based on the brain functional image to determine a functional connection value between the whole brain and a lesion region;

a cross-correlation and out-of-order correlation value calculation unit configured to calculate cross-correlation and out-of-order correlation values between the average signal and the signals of the rest of the whole brain using the cross-correlation verification method;

a functional significant disconnection network determination unit of lesions corresponding to healthy control groups configured to retain a cross-correlation value more than 100 times the out-of-order correlation value as a first cross-correlation value, and take a functional connection value of a position corresponding to the first cross-correlation value as a functional significant disconnection network of the lesions corresponding to the healthy control groups; and a functional significant disconnection network construction unit corresponding to lesions configured to construct the functional significant disconnection network corresponding to the lesions according to the functional significant disconnection network of the lesions corresponding to all of the healthy control groups.

According to specific embodiments provided by the present disclosure, the present disclosure discloses the following technical effects. The present disclosure provides a method and system for extracting a multi-dimensional disconnection network region of symptom mapping. By the method combining single lesion analysis with human brain connectomics, the structural disconnection weighting network and the functional significant disconnection network of the lesions are constructed using the fiber tracking method and the cross-correlation verification method, so as to obtain the multi-dimensional disconnection network region of the lesions. Based on the multi-dimensional disconnection network region of the lesions, the relationship between the lesions and the injury location of the brain system can be accurately reflected, and the injury location of the brain system can be quickly determined, avoiding the error of the "lesion-symptom" relationship of the single lesion analysis method, and improving the accuracy of the mapping between the symptoms and the lesions.

BRIEF DESCRIPTION OF THE DRAWINGS

To describe the technical solutions in the embodiments of the present disclosure or in the prior art more clearly, the accompanying drawings required for the embodiments are briefly described below. Apparently, the accompanying drawings in the following description show merely some embodiments of the present disclosure, and those of ordinary skill in the art may still derive other accompanying drawings from these accompanying drawings without creative efforts.

DETAILED DESCRIPTION

The technical solutions of the embodiments of the present disclosure are clearly and completely described below with reference to the accompanying drawings. Apparently, the described embodiments are merely a part rather than all of the embodiments of the present disclosure. All other embodiments obtained by those of ordinary skill in the art based on the embodiments of the present disclosure without creative efforts shall fall within the protection scope of the present disclosure.

An objective of the present disclosure is to provide a method and system for extracting a multi-dimensional disconnection network region of symptom mapping, so as to improve accuracy of mapping between symptoms and lesions, and accurately locate the lesions according to the symptoms.

To make the above-mentioned objective, features, and advantages of the present disclosure clearer and more comprehensible, the present disclosure will be further described in detail below in conjunction with the accompanying drawings and specific embodiments.

Figure 1:
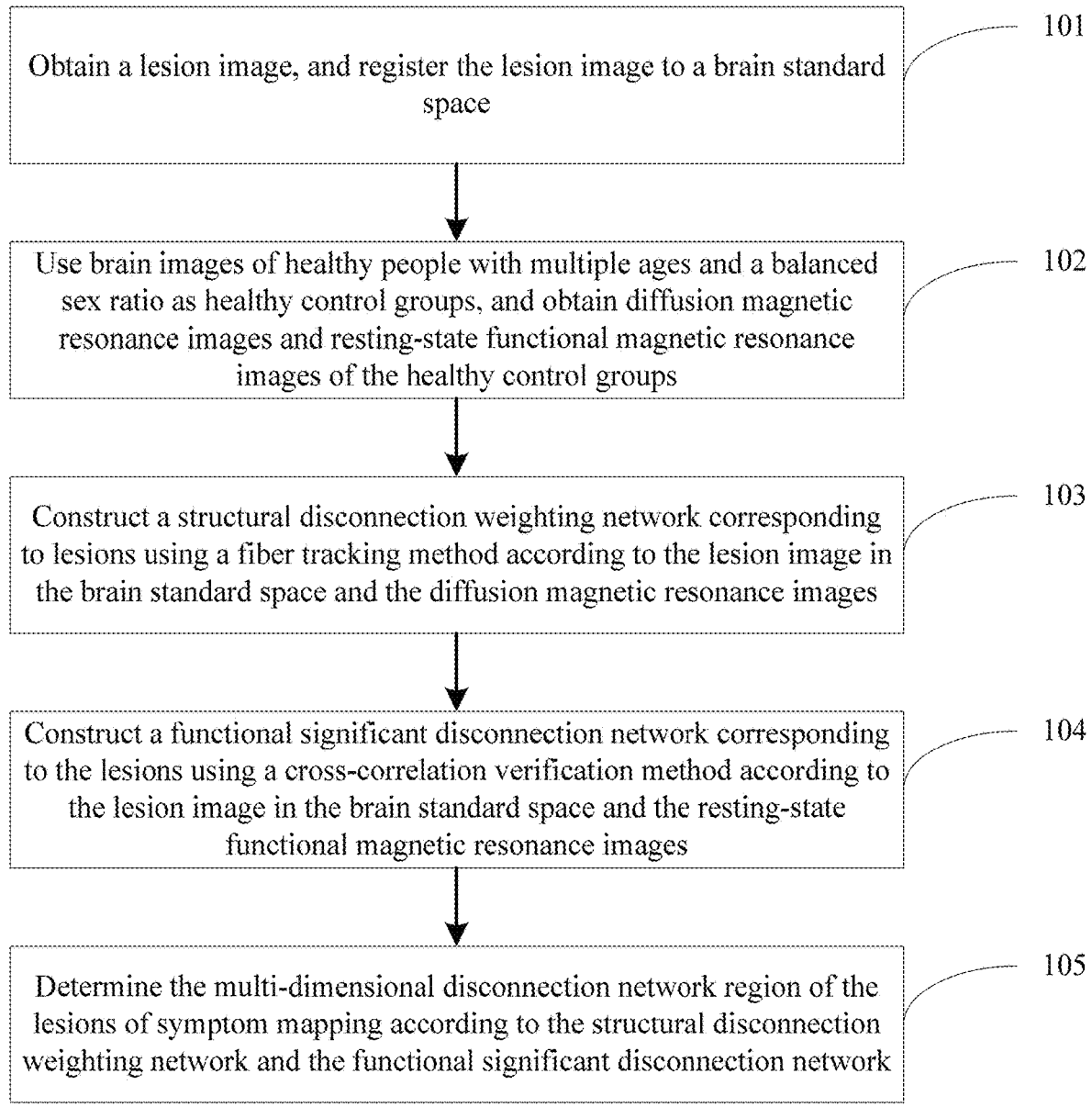
FIG. 1 is a flow chart of a method for extracting a multi-dimensional disconnection network region of symptom mapping provided by the present disclosure.

FIG. 1 is a flow chart of a method for extracting a multi-dimensional disconnection network region of symptom mapping provided by the present disclosure. As shown in FIG. 1, the method for extracting a multi-dimensional disconnection network region of symptom mapping includes the following steps.

Step 101: A lesion image is obtained, and the lesion image is registered to a brain standard space.

Step 101 specifically includes: the lesion image is registered to the brain standard space through linear transformation.

Step 102: Brain images of healthy people with multiple ages and a balanced sex ratio are used as healthy control groups, and diffusion magnetic resonance images and resting-state functional magnetic resonance images of the healthy control groups are obtained.

Step 103: A structural disconnection weighting network corresponding to lesions is constructed using a fiber tracking method according to the lesion image in the brain standard space and the diffusion magnetic resonance images. The fiber tracking method includes deterministic fiber tracking and probabilistic fiber tracking.

Step 103 specifically includes: pre-processing and diffusion weighted imaging modeling are performed on the diffusion magnetic resonance images, and fiber tracking is performed using the fiber tracking method to construct deterministic and probabilistic fiber tracking structural connection images in individual spaces of the healthy control groups. The lesion image in the brain standard space is registered to an individual space of the healthy control group through linear transformation for any of the healthy control groups, and a structural connection image of the lesions is extracted according to the deterministic and probabilistic fiber tracking structural connection images. A weighted average of the structural connection image of the lesions is calculated to determine a structural disconnection weighting network in the individual spaces. The structural disconnection weighting network in the individual spaces is registered to the brain standard space through linear transformation to determine a structural disconnection weighting network of the lesions corresponding to the healthy control groups. The structural disconnection weighting network corresponding to the lesions is constructed according to the structural disconnection weighting network of the lesions corresponding to all of the healthy control groups.

Figure 2:
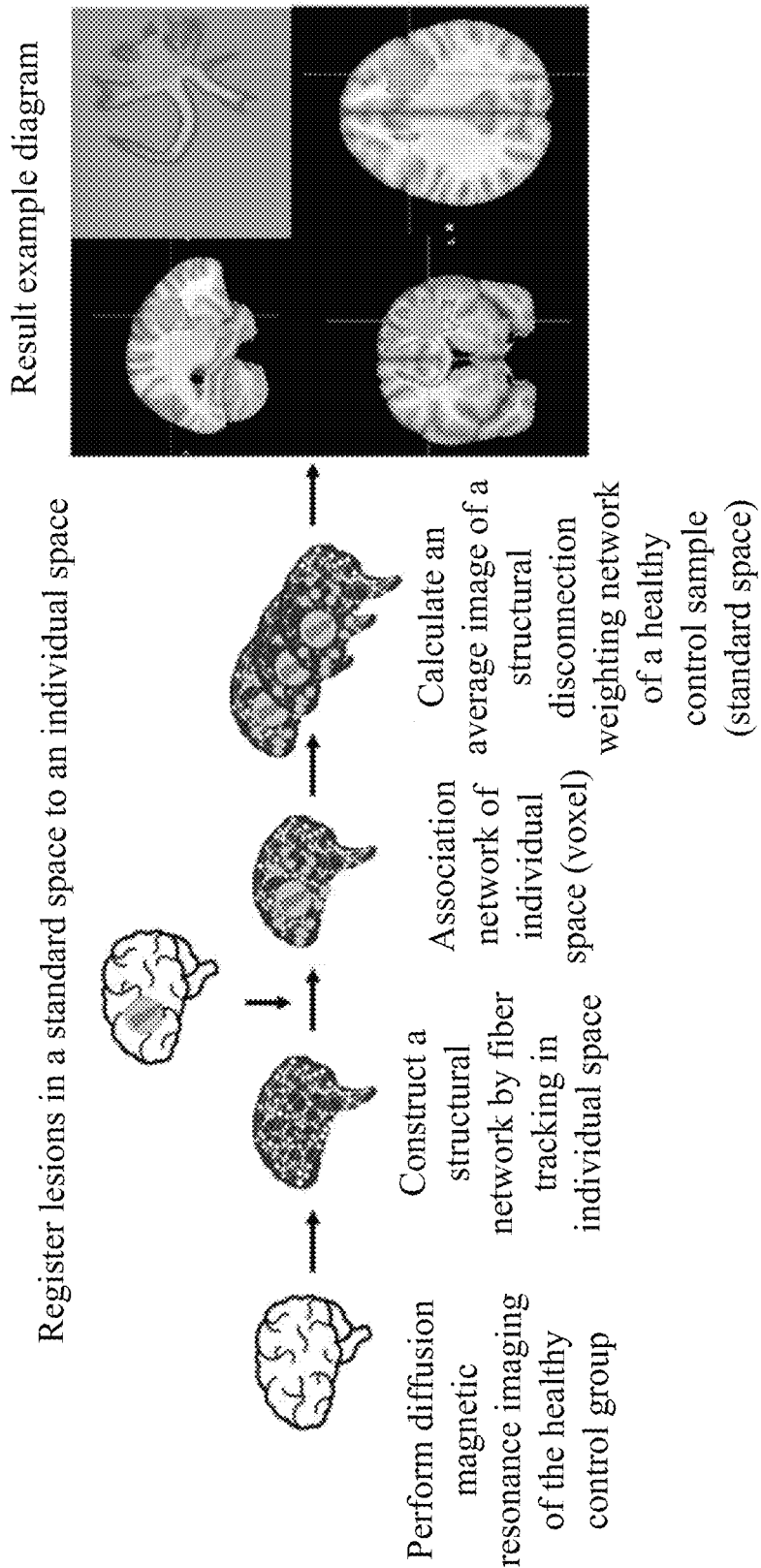
FIG. 2 is a flow chart of construction of a structural disconnection weighting network corresponding to lesions provided by the present disclosure.

In practical application, FIG. 2 is a flow chart of construction of a structural disconnection weighting network corresponding to lesions provided by the present disclosure. As shown in FIG. 2, construction of the structural disconnection weighting network corresponding to the lesions includes the following processes.

1) The lesion image is registered to the brain standard space (i.e., MNI152 standard space) of the Montreal Neurosciences Institute (MNI) through linear transformation.
2) Pre-processing and diffusion weighted imaging modeling are performed on the diffusion magnetic resonance images of the healthy control group with a total of N samples, and fiber tracking is performed. The specific process includes: image format conversion from digital imaging and communications in medicine (DICOM) to neuroimaging informatics technology initiative (NII), image resampling, skull stripping of b0 image, eddy current correction, smoothing, diffusion weighted imaging modeling, deterministic fiber tracking, and probabilistic fiber tracking. Finally, the deterministic and probabilistic fiber tracking structural connection images in the individual space of the healthy control group are constructed.
3) The lesion image in the MNI152 standard space is registered to the individual space of the healthy control group through linear transformation for a sample of the healthy control group, and a structural connection image of the lesions is extracted according to the deterministic and probabilistic fiber tracking results of the individual space of the healthy control group. A weighted average is calculated to obtain a structural disconnection weighting network in the individual space.
4) The structural disconnection weighting network in the individual space of the healthy control group is registered to the MNI152 standard space through linear transformation to obtain a structural disconnection weighting network of the lesions corresponding to the healthy control group.
5) The above processes 3) to 4) are repeated for each image of the healthy control group to obtain a structural disconnection weighting network in a total of N standard spaces, and its average image is calculated. The final structural disconnection weighting network corresponding to the lesions is obtained after MNI152 standard mask overlap calculation.

It should be noted that the final structural disconnection weighting network corresponding to the lesions is in MNI152 standard spatial data format, with a voxel range of 0-1, representing the structural connection strength of each voxel and the lesions.

Step 104: A functional significant disconnection network corresponding to the lesions is constructed using a cross-correlation verification method according to the lesion image in the brain standard space and the resting-state functional magnetic resonance images.

Step 104 specifically includes: the resting-state functional magnetic resonance images are pre-processed to determine a brain functional signal image in the brain standard space. An average signal of a range of the lesions is extracted by taking the lesion image as a ROI in the brain standard space. Pearson correlation between the average signal and signals of the rest of the whole brain is performed based on the brain functional image to determine a functional connection value between the whole brain and a lesion region. Cross-correlation and out-of-order correlation values between the average signal and the signals of the rest of the whole brain are calculated using the cross-correlation verification method. A cross-correlation value more than 100 times the out-of-order correlation value is retained as a first cross-correlation value, and a functional connection value of a position corresponding to the first cross-correlation value is taken as a functional significant disconnection network of the lesions corresponding to the healthy control group. The functional significant disconnection network corresponding to the lesions is constructed according to the functional significant disconnection network of the lesions corresponding to all of the healthy control groups.

Figure 3:
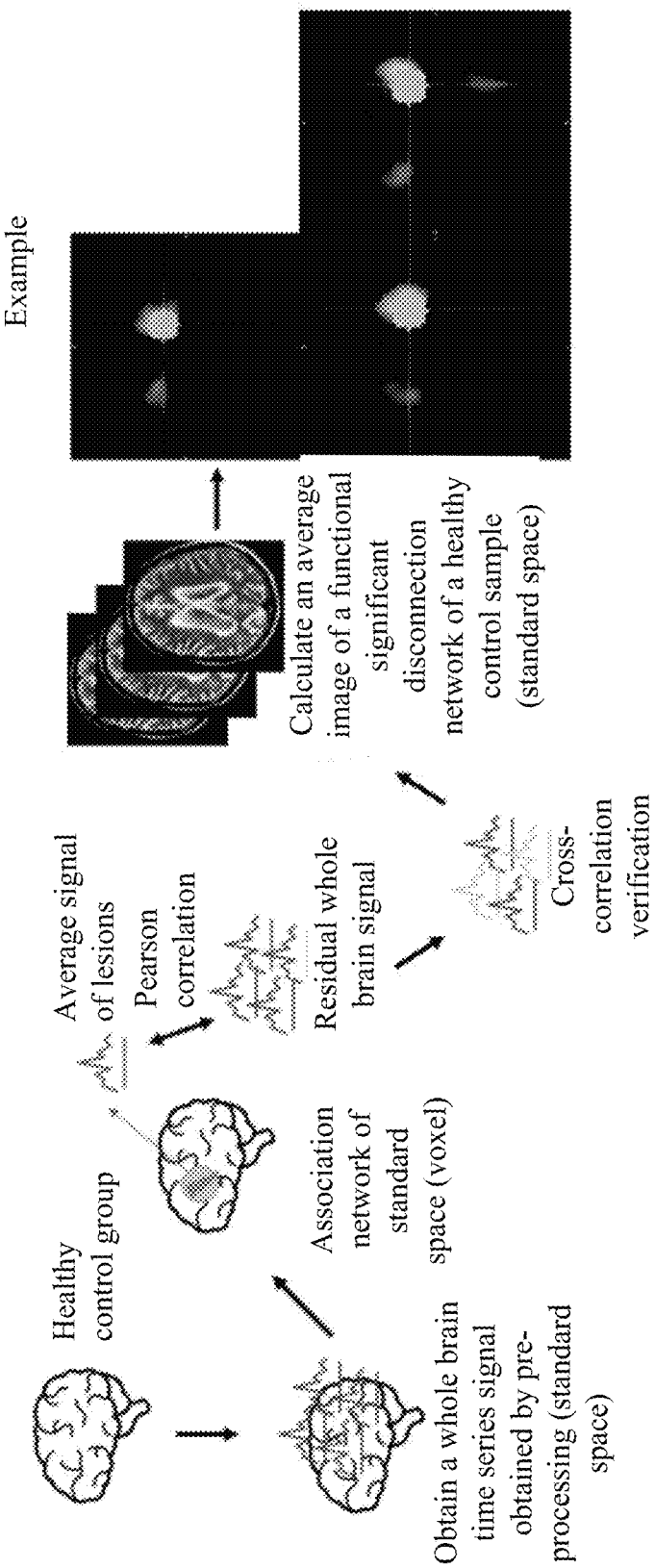
FIG. 3 is a flow chart of construction of a functional significant disconnection network corresponding to the lesions provided by the present disclosure.

In practical application, FIG. 3 is a flow chart of construction of a functional significant disconnection network corresponding to the lesions provided by the present disclosure. As shown in FIG. 3, construction of the functional significant disconnection network corresponding to the lesions includes the following processes.

1) The lesion image is registered to the brain standard space (i.e., MNI152 standard space) of the MNI through linear transformation.
2) The resting-state functional magnetic resonance images of the healthy control group with a total of N samples are pre-processed. The specific process includes: image format conversion from DICOM to NII, removal of unstable time points, time layer correction, head motion correction, spatial standardization, de-linear drift, spatial smoothing, removal of noise variables, and filtering. Finally, the brain functional signal image in the brain standard space is obtained.
3) An average signal of a range of the lesions is extracted by taking the lesion image as a ROI in the brain standard space.
4) Pearson correlation between the average signal extracted in the above step and signals of the rest of the whole brain is performed to calculate a functional connection value between the whole brain and a lesion region.
5) A cross-correlation value and a corresponding out-of-order correlation value between the average signal of a range of the lesions and the signals of the rest of the whole brain are calculated using the cross-correlation verification method. A cross-correlation value more than 100 times the out-of-order correlation value is retained, and a functional connection value of a position corresponding to the cross-correlation value is taken as a final functional significant disconnection network of the lesions corresponding to the healthy control group.
6) The above processes 3 to 5 are repeated for each image of the healthy control group to obtain a functional significant disconnection network in a total of N brain standard spaces, and its average image is calculated. The final functional significant disconnection network corresponding to the lesions is obtained after MNI152 standard mask overlap calculation.

It should be noted that the final functional significant disconnection network of the lesions is in MNI152 standard spatial data format, with a voxel range of 0-1, representing the functional connection strength of each voxel and the lesions.

Step 105: The multi-dimensional disconnection network region of the lesions of symptom mapping is determined according to the structural disconnection weighting network and the functional significant disconnection network. The multi-dimensional disconnection network region of the lesions is configured to locate network mapping of a brain lesion in the brain.

Figure 4:
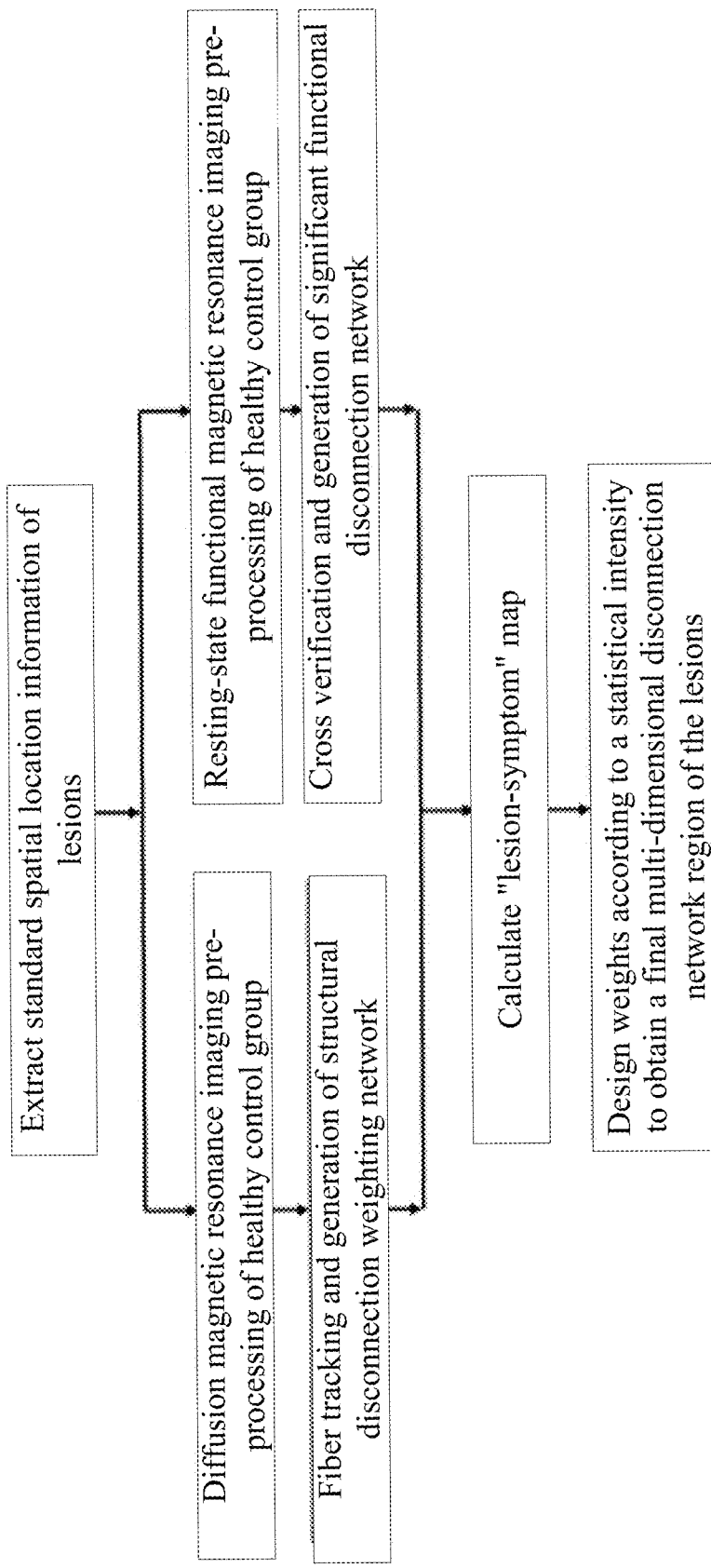
FIG. 4 is a main work flow chart provided by the present disclosure.

In practical application, through steps 103 to 104, the present disclosure obtains the structural disconnection weighting network and functional significant disconnection network corresponding to the lesions. In order to reflect the characteristics of brain disconnection more comprehensively, the lesion itself can also be added to the brain atlas of brain disconnection network as a disconnection signal. Specifically, according to clinical symptom indicators and lesion images, chi square test is performed to obtain lesion regions with significant statistical effect. Subsequently, according to the specific clinical indicators, the group level two-sample t-test statistical analysis is performed, and multiple comparison and correction are performed. The structural disconnection weighting network and functional significant disconnection network with significant statistical effects are selected. Finally, based on the above three disconnected information maps and their respective statistical effect strength, three weight parameters, $\alpha$, $\beta$, and $\gamma$, are designed to be weighted, and finally the multi-dimensional disconnection network region of the lesions corresponding to the specific symptom is obtained through combination. FIG. 4 is a main work flow chart provided by the present disclosure.

Figure 5:
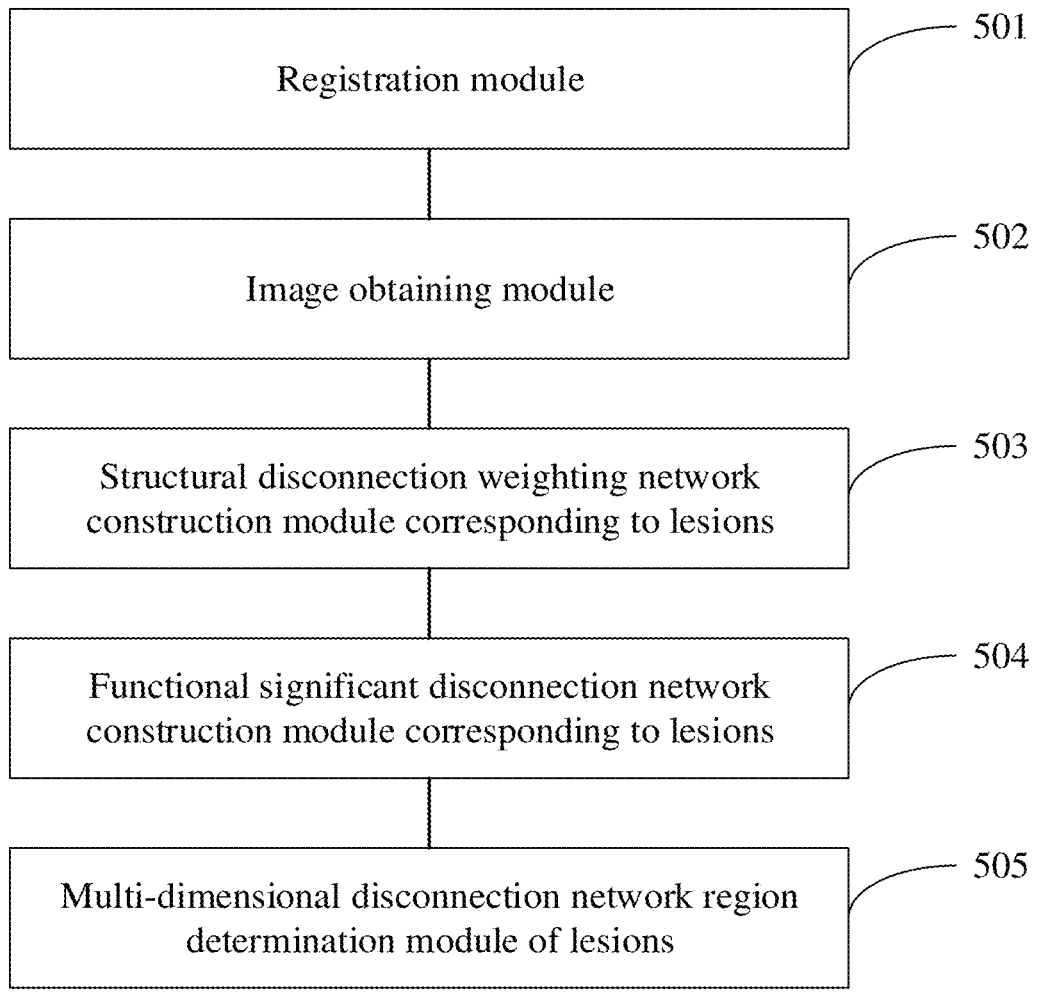
FIG. 5 is a structural diagram of a system for extracting a multi-dimensional disconnection network region of symptom mapping provided by the present disclosure.

FIG. 5 is a structural diagram of a system for extracting a multi-dimensional disconnection network region of symptom mapping provided by the present disclosure. The system for extracting a multi-dimensional disconnection network region of symptom mapping includes: a registration module 501, an image obtaining module 502, a structural disconnection weighting network construction module corresponding to lesions 503, a functional significant disconnection network construction module corresponding to lesions 504, and a multi-dimensional disconnection network region determination module of lesions 505.

The registration module 501 is configured to obtain a lesion image, and register the lesion image to a brain standard space.

Figure 6:
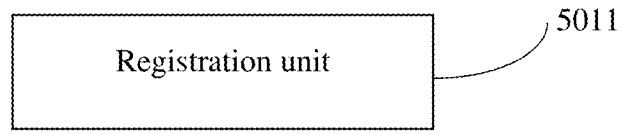
FIG. 6 is a structural diagram of a registration module provided by the present disclosure.

As shown in FIG. 6, the registration module 501 specifically includes: a registration unit 5011 configured to register the lesion image to the brain standard space through linear transformation.

The image obtaining module 502 is configured to use brain images of healthy people with multiple ages and a balanced sex ratio as healthy control groups, and obtain diffusion magnetic resonance images and resting-state functional magnetic resonance images of the healthy control groups.

The structural disconnection weighting network construction module corresponding to lesions 503 is configured to construct a structural disconnection weighting network corresponding to lesions using a fiber tracking method according to the lesion image in the brain standard space and the diffusion magnetic resonance images. The fiber tracking method includes deterministic fiber tracking and probabilistic fiber tracking.

Figure 7:
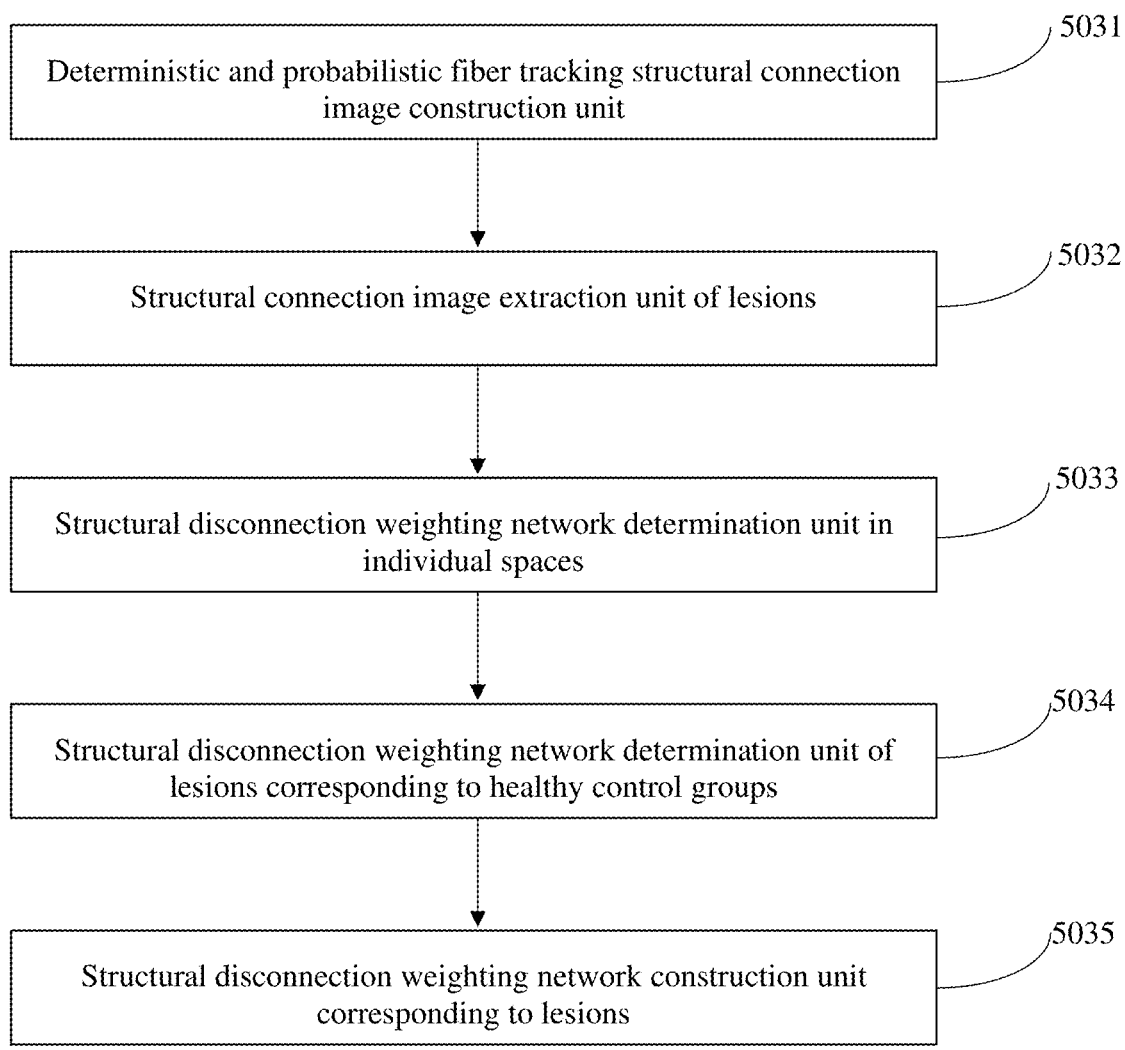
FIG. 7 is a structural diagram of a structural disconnection weighting network construction module corresponding to lesions provided by the present disclosure.

As shown in FIG. 7, the structural disconnection weighting network construction module corresponding to lesions 503 specifically includes: a deterministic and probabilistic fiber tracking structural connection image construction unit 5031, a structural connection image extraction unit of lesions 5032, a structural disconnection weighting network determination unit in individual spaces 5033, a structural disconnection weighting network determination unit of lesions corresponding to healthy control groups 5034, and a structural disconnection weighting network construction unit corresponding to lesions 5035. The deterministic and probabilistic fiber tracking structural connection image construction unit 5031 is configured to perform pre-processing and diffusion weighted imaging modeling on the diffusion magnetic resonance images, and perform fiber tracking using the fiber tracking method to construct deterministic and probabilistic fiber tracking structural connection images in individual spaces of the healthy control groups. The structural connection image extraction unit of lesions 5032 is configured to register the lesion image in the brain standard space to an individual space of the healthy control group through linear transformation for any of the healthy control groups, and extract a structural connection image of the lesions according to the deterministic and probabilistic fiber tracking structural connection images. The structural disconnection weighting network determination unit in individual spaces 5033 is configured to calculate a weighted average of the structural connection image of the lesions to determine a structural disconnection weighting network in the individual spaces. The structural disconnection weighting network determination unit of lesions corresponding to healthy control groups 5034 is configured to register the structural disconnection weighting network in the individual spaces to the brain standard space through linear transformation to determine a structural disconnection weighting network of the lesions corresponding to the healthy control groups. The structural disconnection weighting network construction unit corresponding to lesions 5035 is configured to construct the structural disconnection weighting network corresponding to the lesions according to the structural disconnection weighting network of the lesions corresponding to all of the healthy control groups.

The functional significant disconnection network construction module corresponding to lesions 504 is configured to construct a functional significant disconnection network corresponding to the lesions using a cross-correlation verification method according to the lesion image in the brain standard space and the resting-state functional magnetic resonance images.

Figure 8:
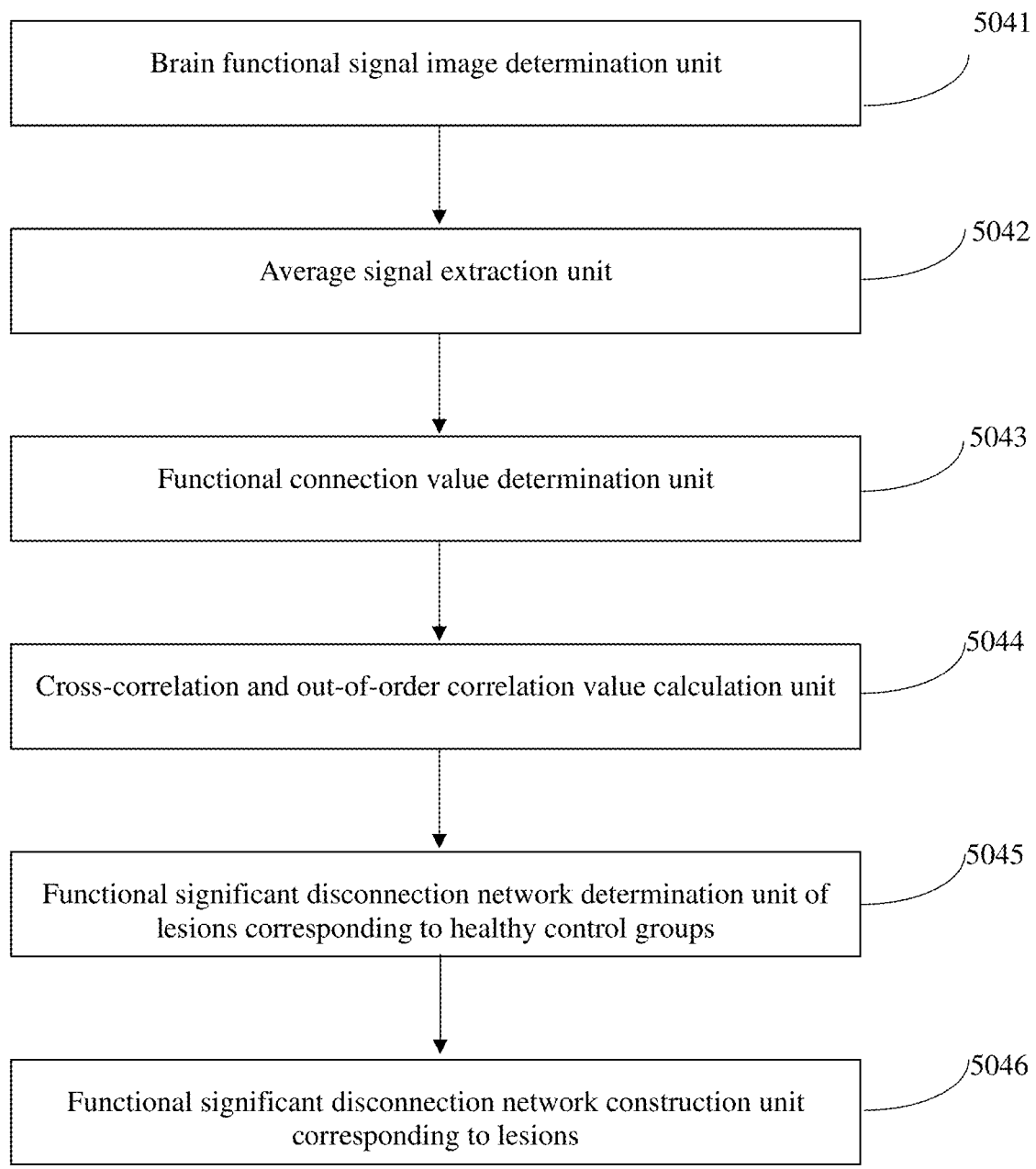
FIG. 8 is a structural diagram of a functional significant disconnection network construction module corresponding to lesions provided by the present disclosure.

As shown in FIG. 8, the functional significant disconnection network construction module corresponding to lesions 504 specifically includes: a brain functional signal image determination unit 5041, an average signal extraction unit 5042, a functional connection value determination unit 5043, a cross-correlation and out-of-order correlation value calculation unit 5044, a functional significant disconnection network determination unit of lesions corresponding to healthy control groups 5045, and a functional significant disconnection network construction unit corresponding to lesions 5046. The brain functional signal image determination unit 5041 is configured to pre-process the resting-state functional magnetic resonance images to determine a brain functional signal image in the brain standard space. The average signal extraction unit 5042 is configured to extract an average signal of a range of the lesions by taking the lesion image as a ROI in the brain standard space. The functional connection value determination unit 5043 is configured to perform Pearson correlation between the average signal and signals of the rest of the whole brain based on the brain functional image to determine a functional connection value between the whole brain and a lesion region. The cross-correlation and out-of-order correlation value calculation unit 5044 is configured to calculate cross-correlation and out-of-order correlation values between the average signal and the signals of the rest of the whole brain using the cross-correlation verification method. The functional significant disconnection network determination unit of lesions corresponding to healthy control groups 5045 is configured to retain a cross-correlation value more than 100 times the out-of-order correlation value as a first cross-correlation value, and take a functional connection value of a position corresponding to the first cross-correlation value as a functional significant disconnection network of the lesions corresponding to the healthy control groups. The functional significant disconnection network construction unit corresponding to lesions 5046 is configured to construct the functional significant disconnection network corresponding to the lesions according to the functional significant disconnection network of the lesions corresponding to all of the healthy control groups.

The multi-dimensional disconnection network region determination module of lesions 505 is configured to determine the multi-dimensional disconnection network region of the lesions of symptom mapping according to the structural disconnection weighting network and the functional significant disconnection network. The multi-dimensional disconnection network region of the lesions is configured to locate network mapping of a brain lesion in the brain.

The present disclosure adopts healthy people with multiple ages and a balanced sex ratio as the control group, and the brain connection information has representative significance of the population, and can more accurately reflect the injury of the brain system caused by the lesions.

The present disclosure only requires the location information in the brain standard space for the lesion image, so it has excellent interface generalization and clinical adaptability, and can be applied to the complex situations with different imaging systems and imaging parameters in clinical practice.

The multi-dimensional disconnection network region of the lesions provided by the present disclosure is an objective indicator. When it is used for evaluating the severity of the lesion, it does not depend on the subjective judgment of medical staff, and can avoid the outcome difference caused by different people.

The brain is regarded as a complex system with interconnected basic units, and based on connectomic thinking, the present disclosure aims to explore the network mechanism behind lesion injury from the perspective of network, so as to make up the analysis level that cannot be covered by the single-lesion symptom mapping analysis technology, and provide more comprehensive analysis information for the study of "lesion-symptom" mapping association.

The embodiments of the present specification are described in a progressive manner, each embodiment focuses on the difference from other embodiments, and the same and similar parts between the embodiments may refer to each other. Since the system disclosed in an embodiment corresponds to the method disclosed in another embodiment, the description is relatively simple, and reference can be made to the method description.

Specific examples are used herein to explain the principles and embodiments of the present disclosure. The foregoing description of the embodiments is merely intended to help understand the method of the present disclosure and its core ideas; besides, various modifications may be made by those of ordinary skill in the art to specific embodiments and the scope of application in accordance with the ideas of the present disclosure. In conclusion, the content of the present specification shall not be construed as limitations to the present disclosure.

What is claimed is:

1. A method for extracting a multi-dimensional disconnection network region of symptom mapping, comprising:
    obtaining a lesion image, and registering the lesion image to a brain standard space;
    using brain images of healthy people with multiple ages and a balanced sex ratio as healthy control groups, and obtaining diffusion magnetic resonance images and resting-state functional magnetic resonance images of the healthy control groups;
    constructing a structural disconnection weighting network corresponding to lesions using a fiber tracking method according to the lesion image in the brain standard space and the diffusion magnetic resonance images, wherein the fiber tracking method comprises deterministic fiber tracking and probabilistic fiber tracking;
    constructing a functional significant disconnection network corresponding to the lesions using a cross-correlation verification method according to the lesion image in the brain standard space and the resting-state functional magnetic resonance images; and
    determining the multi-dimensional disconnection network region of the lesions of symptom mapping according to the structural disconnection weighting network and the functional significant disconnection network, wherein the multi-dimensional disconnection network region of the lesions is configured to locate network mapping of a brain lesion in the brain.

2. The method for extracting a multi-dimensional disconnection network region of symptom mapping according to claim 1, wherein a process of registering the lesion image to a brain standard space specifically comprises:
    registering the lesion image to the brain standard space through linear transformation.

3. The method for extracting a multi-dimensional disconnection network region of symptom mapping according to claim 1, wherein a process of constructing a structural disconnection weighting network corresponding to lesions using a fiber tracking method according to the lesion image in the brain standard space and the diffusion magnetic resonance images specifically comprises:
    performing pre-processing and diffusion weighted imaging modeling on the diffusion magnetic resonance images, and performing fiber tracking using the fiber tracking method to construct deterministic and probabilistic fiber tracking structural connection images in individual spaces of the healthy control groups;
    registering the lesion image in the brain standard space to an individual space of the healthy control group through linear transformation for any of the healthy control groups, and extracting a structural connection image of the lesions according to the deterministic and probabilistic fiber tracking structural connection images;

calculating a weighted average of the structural connection image of the lesions to determine a structural disconnection weighting network in the individual spaces;

registering the structural disconnection weighting network in the individual spaces to the brain standard space through linear transformation to determine a structural disconnection weighting network of the lesions corresponding to the healthy control groups; and constructing the structural disconnection weighting network corresponding to the lesions according to the structural disconnection weighting network of the lesions corresponding to all of the healthy control groups.

4. The method for extracting a multi-dimensional disconnection network region of symptom mapping according to claim 1, wherein a process of constructing a functional significant disconnection network corresponding to the lesions using a cross-correlation verification method according to the lesion image in the brain standard space and the resting-state functional magnetic resonance images specifically comprises:

pre-processing the resting-state functional magnetic resonance images to determine a brain functional signal image in the brain standard space;

extracting an average signal of a range of the lesions by taking the lesion image as a region of interest (ROI) in the brain standard space;

performing Pearson correlation between the average signal and signals of the rest of the whole brain based on the brain functional image to determine a functional connection value between the whole brain and a lesion region;

calculating cross-correlation and out-of-order correlation values between the average signal and the signals of the rest of the whole brain using the cross-correlation verification method;

retaining a cross-correlation value more than 100 times the out-of-order correlation value as a first cross-correlation value, and taking a functional connection value of a position corresponding to the first cross-correlation value as a functional significant disconnection network of the lesions corresponding to the healthy control groups; and constructing the functional significant disconnection network corresponding to the lesions according to the functional significant disconnection network of the lesions corresponding to all of the healthy control groups.

5. A system for extracting a multi-dimensional disconnection network region of symptom mapping, comprising:

a registration module configured to obtain a lesion image, and register the lesion image to a brain standard space;

an image obtaining module configured to use brain images of healthy people with multiple ages and a balanced sex ratio as healthy control groups, and obtain diffusion magnetic resonance images and resting-state functional magnetic resonance images of the healthy control groups;

a structural disconnection weighting network construction module corresponding to lesions configured to construct a structural disconnection weighting network corresponding to lesions using a fiber tracking method according to the lesion image in the brain standard space and the diffusion magnetic resonance images, wherein the fiber tracking method comprises deterministic fiber tracking and probabilistic fiber tracking;

a functional significant disconnection network construction module corresponding to lesions configured to construct a functional significant disconnection network corresponding to the lesions using a cross-correlation verification method according to the lesion image in the brain standard space and the resting-state functional magnetic resonance images; and a multi-dimensional disconnection network region determination module of lesions configured to determine the multi-dimensional disconnection network region of the lesions of symptom mapping according to the structural disconnection weighting network and the functional significant disconnection network, wherein the multi-dimensional disconnection network region of the lesions is configured to locate network mapping of a brain lesion in the brain.

6. The system for extracting a multi-dimensional disconnection network region of symptom mapping according to claim 5, wherein the registration module specifically comprises:

a registration unit configured to register the lesion image to the brain standard space through linear transformation.

7. The system for extracting a multi-dimensional disconnection network region of symptom mapping according to claim 5, wherein the structural disconnection weighting network construction module corresponding to lesions specifically comprises:

a deterministic and probabilistic fiber tracking structural connection image construction unit configured to perform pre-processing and diffusion weighted imaging modeling on the diffusion magnetic resonance images, and perform fiber tracking using the fiber tracking method to construct deterministic and probabilistic fiber tracking structural connection images in individual spaces of the healthy control groups;

a structural connection image extraction unit of lesions configured to register the lesion image in the brain standard space to an individual space of the healthy control group through linear transformation for any of the healthy control groups, and extract a structural connection image of the lesions according to the deterministic and probabilistic fiber tracking structural connection images;

a structural disconnection weighting network determination unit in individual spaces configured to calculate a weighted average of the structural connection image of the lesions to determine a structural disconnection weighting network in the individual spaces;

a structural disconnection weighting network determination unit of lesions corresponding to healthy control groups configured to register the structural disconnection weighting network in the individual spaces to the brain standard space through linear transformation to determine a structural disconnection weighting network of the lesions corresponding to the healthy control groups; and a structural disconnection weighting network construction unit corresponding to lesions configured to construct the structural disconnection weighting network corresponding to the lesions according to the structural disconnection weighting network of the lesions corresponding to all of the healthy control groups.

8. The system for extracting a multi-dimensional disconnection network region of symptom mapping according to claim 5, wherein the functional significant disconnection network construction module corresponding to lesions specifically comprises:
- a brain functional signal image determination unit configured to pre-process the resting-state functional magnetic resonance images to determine a brain functional signal image in the brain standard space;
- an average signal extraction unit configured to extract an average signal of a range of the lesions by taking the lesion image as a ROI in the brain standard space;
- a functional connection value determination unit configured to perform Pearson correlation between the average signal and signals of the rest of the whole brain based on the brain functional image to determine a functional connection value between the whole brain and a lesion region;
- a cross-correlation and out-of-order correlation value calculation unit configured to calculate cross-correlation and out-of-order correlation values between the average signal and the signals of the rest of the whole brain using the cross-correlation verification method;
- a functional significant disconnection network determination unit of lesions corresponding to healthy control groups configured to retain a cross-correlation value more than 100 times the out-of-order correlation value as a first cross-correlation value, and take a functional connection value of a position corresponding to the first cross-correlation value as a functional significant disconnection network of the lesions corresponding to the healthy control groups; and a functional significant disconnection network construction unit corresponding to lesions configured to construct the functional significant disconnection network corresponding to the lesions according to the functional significant disconnection network of the lesions corresponding to all of the healthy control groups.

* * * * *